US009861994B2

(12) United States Patent
Safarik et al.

(10) Patent No.: US 9,861,994 B2
(45) Date of Patent: Jan. 9, 2018

(54) SYSTEMS, METHODS, AND APPARATUSES FOR PROVIDING VISCOUS FLUID IN A PARTICULAR FORMAT AND IMPLEMENTATIONS THEREOF

(71) Applicants: Charles Robert Safarik, Wesley Chapel, FL (US); Prashanth Sridharan, Dunedin, FL (US)

(72) Inventors: Charles Robert Safarik, Wesley Chapel, FL (US); Prashanth Sridharan, Dunedin, FL (US)

(*) Notice: Subject to any disclaimer, the term of this patent is extended or adjusted under 35 U.S.C. 154(b) by 349 days.

(21) Appl. No.: 14/223,901

(22) Filed: Mar. 24, 2014

(65) Prior Publication Data
US 2014/0283919 A1    Sep. 25, 2014

Related U.S. Application Data

(60) Provisional application No. 61/804,563, filed on Mar. 22, 2013.

(51) Int. Cl.
| B05B 7/04 | (2006.01) |
| B05B 7/06 | (2006.01) |
| F17D 3/01 | (2006.01) |

(52) U.S. Cl.
CPC .......... *B05B 7/0483* (2013.01); *B05B 7/0491* (2013.01); *B05B 7/064* (2013.01); *B05B 7/067* (2013.01); *F17D 3/01* (2013.01); *Y10T 137/0391* (2015.04)

(58) Field of Classification Search
CPC ... B05B 7/0466; B05B 7/0475; B05B 7/0483; B05B 7/0491; B05B 7/062; B05B 7/064; B05B 7/066; B05B 7/067; B05B 7/068
See application file for complete search history.

(56) References Cited

U.S. PATENT DOCUMENTS

| 3,531,050 A * | 9/1970 | Abraham .............. B05B 7/0441 239/427.3 |
| 3,601,516 A | 8/1971 | Somhegyi |
| 3,897,007 A * | 7/1975 | Roy ...................... B05B 7/0441 239/403 |
| 6,174,160 B1 * | 1/2001 | Lee ....................... F23D 11/007 239/13 |

(Continued)

OTHER PUBLICATIONS

International Search Report and Written Opinion of the International Searching Authority for PCT/US 14/31627 dated Aug. 12, 2014.

*Primary Examiner* — Ryan Reis
(74) *Attorney, Agent, or Firm* — Miles & Stockbridge P.C.; David R. Schaffer

(57) ABSTRACT

The present invention involves providing a viscous fluid in a particular format and implementations thereof. In particular, a viscous slave fluid is provided in a particular format, wherein the particular format can be an end result or an intermediate result for the viscous fluid. In the case of an intermediate result, the viscous fluid in the second format may be further processed to a third format. Implementations or applications include supercharged fuel injection systems, methods, and apparatuses for internal combustion, lean-burn oil pre-mixing systems, methods, and apparatuses for liquid fuel combustion, and medical or biomedical devices, systems, and methods.

21 Claims, 5 Drawing Sheets

(56) References Cited

U.S. PATENT DOCUMENTS

| | | | |
|---|---|---|---|
| 6,379,146 B1* | 4/2002 | Zink | F23D 14/085 110/262 |
| 8,448,879 B2* | 5/2013 | Krug | B05B 7/00 239/132.3 |
| 2003/0114791 A1 | 6/2003 | Rosenthal | |
| 2007/0278328 A1* | 12/2007 | Bartolini | B01B 1/005 239/427 |

* cited by examiner

SYSTEMS, METHODS, AND APPARATUSES FOR PROVIDING VISCOUS FLUID IN A PARTICULAR FORMAT AND IMPLEMENTATIONS THEREOF

CROSS-REFERENCE TO RELATED APPLICATIONS

This application is a continuation of Application No. 61/804,563 filed Mar. 22, 2013 including the specification, drawings and abstract which is hereby incorporated herein by reference in its entirety.

TECHNICAL AREA

Generally speaking, embodiments of the present invention are directed to providing a viscous fluid in a particular format and implementations thereof. More specifically, embodiments of the present invention involve production of a viscous slave fluid in a particular format, wherein the particular format can be an end result or an intermediate result for the viscous fluid, for instance a relatively thin, uniform sheet of viscous liquid spread over a certain, predefined area by a first working fluid of twin or dual working fluids. In the case of an intermediate result, the sheet of viscous fluid may be further processed, for example, by a second working fluid of the twin or dual working fluids for atomization.

SUMMARY

The Summary describes and identifies features of some embodiments. It is presented as a convenient summary of some embodiments, but not all.

As will be discussed in more detail below, the present invention entails supercharged fuel injection systems, methods, and apparatuses for internal combustion (e.g., internal diesel combustion). The present invention also entails lean-burn oil pre-mixing systems, methods, and apparatuses, for example, for liquid fuel combustion (e.g., industrial combustion). Embodiments also involve medical applications, such as medical or biomedical devices, systems, and methods (e.g., internal biological surface therapy). Non-limiting examples of embodiments of the present invention are as follows:

Embodiments of the present invention can include (i.e., comprise) a method, device, and system to create a thin sheet from a liquid flow stream, wherein the thin sheet can be flat, cylindrical, half or partial toroidal, arced, curved, linear, or non-linear, for instance, as defined by a corresponding working geometry, for atomizing the thin sheet, while simultaneously pre-mixing with a percentage or percentage range of combustion air for combustion of liquid fuels, for example, a lean-burn pre-mix for an oil flame. The method, device, or system can also attenuate or reduce nitrous oxide formation.

Embodiments of the present invention can also include a method, device, and system to create a thin liquid fuel sheet from a liquid flow stream by utilizing viscous and momentum effects of another fluid (e.g., the acceleration of the fluid) to atomize the thin sheet into droplets. The droplets can be small and can correspond in size to a thinnest portion of the thin liquid sheet. The thin sheet, upon or at atomization, can be pre-mixed with air, for example, combustion air, so as to reduce or attenuate nitrous oxide produced by a subsequent burning or combustion of the air and the fuel. Thus, embodiments of the present invention include a method, device, and system to create the aforementioned pre-mixture of vaporized or atomized liquid fuel and combustion air as a direct result of a flow stream of the liquid fuel being acted upon by an accelerating flow field of another fluid (e.g., air), which causes pre-mixing of the liquid fuel only after the liquid sheet is sufficiently thin to be vaporized or atomized.

Also included in embodiments of the present invention are a method, device, and system of creating a relatively thin liquid sheet which can pre-mix with air to produce a flow field within which a maximum velocity of the sheet and resultant droplets from atomization do not meet or do not exceed a velocity of the working fluid. The thin liquid sheet can be created or formed, by the flow field of another fluid (e.g., air), by a filming or working surface such that the liquid sheet is dragged in the direction of the flow field across and takes the form of the filming or working surface, which may reduce or suppress surface diffusion of the liquid sheet into the flow field of the another fluid.

For example, the liquid flow stream of fuel may be flattened into a thin sheet, which can be acted upon by viscous and pressure forces of an airflow field to partially vaporize the fuel sheet. In other words, the rate of slave fluid film thickness thinning, is related directly to the rate of pressure change along the exit path as the flow accelerates from reduction in flow area. Such example can result in no or minimal pre-aeration prior to full mixing. Put another way, the viscosity and momentum interaction between the two fluids can cause formation of a film which diminishes in thickness along the length of the filming surface and whose surface disturbance can be suppressed by the acceleration of the other fluid, and the compression of the film.

In embodiments, optionally, the filming or working surface can increase in surface area along the direction of flow, for example, to all both axial and lateral distribution of the film, thereby forming a thin sheet. The thin sheet can traverse a path of a predetermined length such whereupon at a certain thickness or thickness range, the sheet can vaporize as it breaks into droplets under the forces of the airflow field to produce a pre-mix ratio of fuel and air for a lean burning environment. Thus, embodiments of the present invention can use an accelerating air flow field to create a sheet of fuel oil, for example, thin enough to allow the sheet of fuel oil to atomize and vaporize and an end of the filing or working surface, for example, under conditions where a maximum fuel oil velocity do not exceed a maximum velocity of the air flow stream at any point, but the fuel sheet does experience acceleration caused by the pre-mixing air flow.

Embodiments of the present invention also include a method, system, and device to create a film by dragging one fluid in a direction of and under the influence of viscous and pressure forces of another fluid to allow deposition of the fluid upon a third surface, for example, as in smearing a coating on the third surface via spray or film transference.

Embodiments of the present invention also include a method, system, and device to create a film by dragging one fluid in a direction of and under the influence of friction between two fluids to allow deposition of the fluid upon a third surface, for example, as in smearing a coating on the third surface via spray or film transference. This embodiment provides finer fuel spray droplets using friction instead of pressure. The droplet size is uniform and less than half the size of the best performance of fuel injectors available today and droplet formation occurs as the fuel mixes with air along the length of the injector. Upon departing from the injector, the fuel and air mix already contains all of the air for optimum combustion, exiting from a circular slot or annulus and into the cylinder. The slot or annulus can be any shape to suit the application and the need for small holes is eliminated. It should be noted that this method does not produce designs that depend upon impingement within the cylinders, or upon the piston. As a result, manufacturing tolerances necessary for producing precision holes and apertures is eliminated. Benefits include: liquid fuel burns similar to gaseous fuel combustion with lower emissions; and engine control methods that are presently used will remain the same.

Embodiments will hereinafter be described in detail below with reference to the accompanying drawings, wherein like reference numerals represent like elements. The accompanying drawings have not necessarily been drawn to scale. Any values dimensions illustrated in the accompanying graphs and figures are for illustration purposes only and may or may not represent actual or preferred values or dimensions. Where applicable, some features may not be illustrated to assist in the description of underlying features.

BRIEF DESCRIPTION OF THE DRAWINGS

Non-limiting and non-exhaustive embodiments of the present invention are described with reference to the following figures, wherein like reference numerals and/or indicia refer to like parts throughout the various views unless otherwise precisely specified.

DETAILED DESCRIPTION

In general, the present invention involves providing a viscous fluid in a particular format and implementations thereof, wherein the particular format can be an end result or an intermediate result for the viscous fluid. As will be discussed in more detail below, the viscous fluid, in its particular format, can be provided in a number of contexts, such as for fuel injection, for lean-burn pre-mixing, and for application of coatings in medical or biomedical applications. In one or more embodiments, the viscosity of the viscous fluid is at or below 200 Saybolt Universal Seconds (SSU).

Production of the viscous slave fluid in the particular format, whether intermediate result and/or end result, can be achieved by action on the slave fluid by one or more working fluids. Specific dynamics of slave and working fluid interaction can produce mixtures or coatings including the slave fluid. For example, one or more embodiments of the present invention can utilize shear and pressure forces associated with a working fluid to transform the slave fluid from a first format to an intermediate format and to a final or end format. In other words, the rate of slave fluid film thickness thinning, is related directly to the rate of pressure change along the exit path as the flow accelerates from reduction in flow area. Optionally, the working fluid may be a twin or dual working fluid. Thus, a working fluid can cause the slave fluid to deform under viscous and pressure forces of the former, for example, to produce a thin sheet of the latter, which can result in pre-mixing of the slave and working fluids, atomization and vaporization of the latter, and formation of a pre-mixed cloud of the slave and working fluids.

Figure 1:
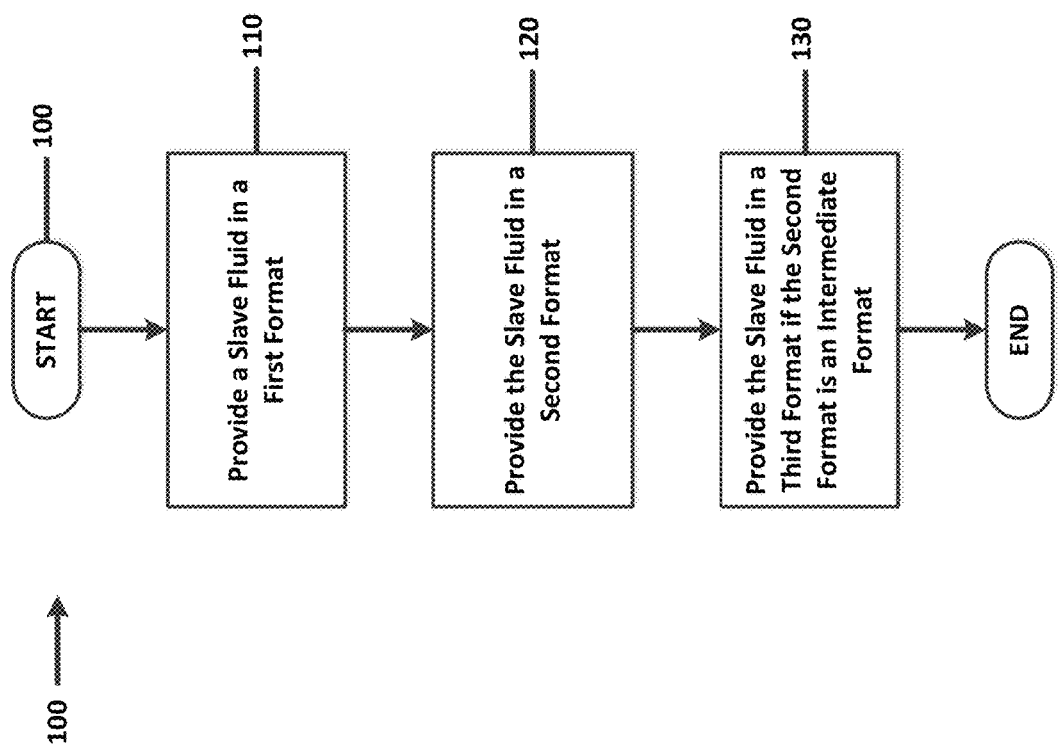
FIG. 1 is a basic flow chart of a method in accordance with one or more embodiments of the present invention.
Figure 2:
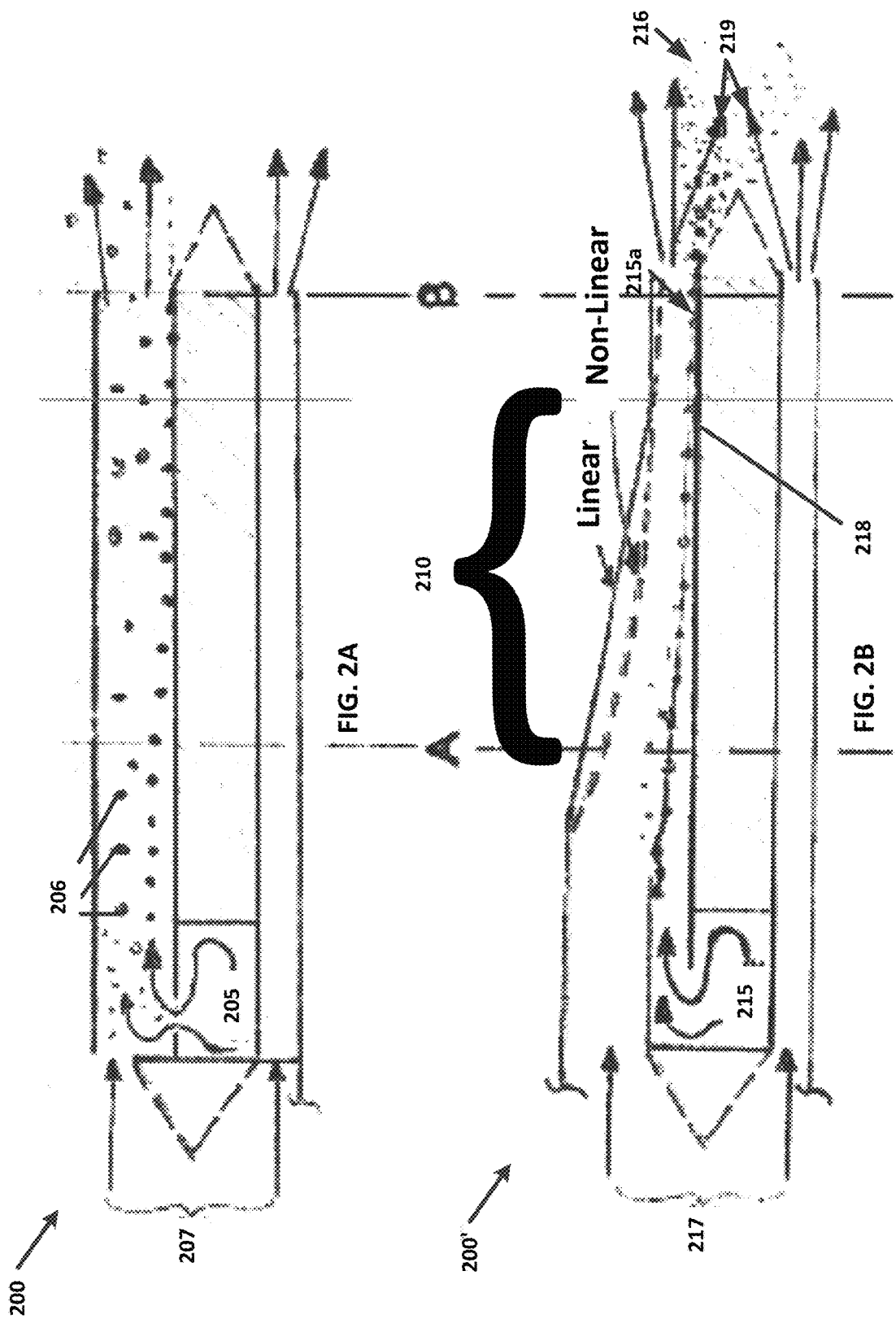
FIG. 2A is a diagrammatic representation of a system studied in development of the present invention.
FIG. 2B is a diagrammatic representation in accordance with one or more embodiments of the present invention.

FIG. 1 is a basic flow chart for a method 100 according to one or more embodiments of the present invention. Generally, method 100 is directed to providing a slave fluid in a particular format or particular formats.

At 110 in method 100, a slave fluid, such as a liquid fuel, is provided in a first format. For example, the slave fluid can be provided in liquid form, as a film or continuous laminar liquid flow, to a first end of a filming surface. Optionally, the slave fluid may be provided to the first end of the filming surface at zero or near zero velocity. The slave fluid optionally can be provided parallel or substantially parallel to the filming surface and/or a flow path of a working fluid. Thus, the slave fluid may be provided to the first end of the filming surface as a film having a first thickness. Further, the film can take the shape of the filming surface at the first end thereof.

At 120 in method 100, the slave fluid can be provided in a second format different from the first format. That is, the slave fluid can be acted upon so as to change it from the first format to the second format. For instance, the second format can be a film or sheet (or even plural films or sheets) having a second thickness less than the first thickness of the slave fluid in the first format, and provided on a second end of the filming surface remote from the first end of the filming surface.

The slave fluid in the second format can be obtained by utilizing shear and pressure forces of a working fluid or fluids while traversing the slave fluid from the first end of the filming surface to the second end of the filming surface. In other words, the rate of slave fluid film thickness thinning, is related directly to the rate of pressure change along the exit path as the flow accelerates from reduction in flow area. For instance, the working fluid can be a twin or dual flow of the working fluid, one flow of which directly shearing the slave film (e.g., complete shearing) and the other flow intersecting the slave film. The working fluid which shears the film can pass through a decreasing flow area, for example, an ever decreasing flow area, which can cause acceleration resulting in a normal force, for example, proportional to the square of the velocity, acting upon the film surface. Further, the pressure distribution along the film surface may deform the slave fluid film or sheet, thereby causing a decrease in its thickness along its path on the filming surface. Optionally, the filming surface area may increase axially and/or transaxially. Further, the filming surface is of predetermined size, particularly a predetermined length with an increasing width, such that the working fluid drags the slave fluid to a minimum desired thickness, for example, a desired diameter (e.g., minimum or maximum) or diameter range of droplets of which the sheet or film may be comprised.

Optionally, the second format may be a "final" format. For example, the slave fluid film or sheet having the second thickness and, for example, pre-mixed with the working fluid, may be output or extruded as a coating, netting, encapsulation, or surface layer, for instance, for a particular application, such as a medical or biomedical application. Alternatively, the second format is not the final format and the slave fluid may be provided in a third format different from the second format. In general, a predetermined final thickness of the second format immediately prior to atomization and/or other output can be 10 to 20 microns.

At 130 in method 100, the slave fluid can be provided in the third format different from the second format. That is, the slave fluid can be acted upon so as to change or transform it from the second format to the third format. For instance, the third format can be a pre-mixture of the working fluid and slave fluid and/or the slave fluid in atomized form with the working fluid. Optionally, pre-mixing and atomization can occur simultaneously or substantially simultaneously.

Further, the pressure (e.g., pressure distribution) in 120 indicated above can be so as to negate or minimize atomization until the film is sufficiently thin (i.e., to prevent or minimize pre-atomization or pre-vaporization) in order that pre-mixing and atomization occur simultaneously or substantially simultaneously. Put another way, a continuous laminar liquid flow can be dragged to a thin film before atomization. Thus, the surface area of the filming surface is of sufficient size, particularly length with increasing width, to delay break up into small particles until the slave film or sheet has dissipated to a predetermined thickness or thickness range at which time the film or sheet can be and mixed with and atomized by the working fluid(s). The particles produced can be relatively smaller in size and can be provided in a uniform distribution of droplet size, which can lead to a reduction in fuel consumption (e.g., 20%-25%) for a same amount of available energy.

Further, unlike systems, apparatuses, and methods which implement air blast effects or jets, for example high pressure or high velocity jets, providing the slave fluid in the third format as set forth in 130 of method 100 and herein can be performed without air blast effects or without high velocity or pressure jets providing air blasts. Thus, relatively low pressure or low velocity fluid, for example air, can be used as an atomizing media. Additionally, embodiments of the present invention may not use micro-holes to provide the slave fluid in the third format, but instead may use an annulus or a plurality of annuli.

Accordingly, embodiments of the method 100, as well as systems, apparatuses, and devices according to embodiments of the present invention, can obtain homogeneity in the slave fluid/-working fluid mixture, can obtain the most uniform distribution of droplet size, can minimize or eliminate impingement and/or splash, and/or can control droplet size and/or velocity Though not expressly shown in FIG. 1, after 130, the slave fluid in the third format can be further processed. For example, the slave fluid (and working fluid) may be applied to a combustion chamber for combustion.

FIG. 2A is a diagrammatic representation of a system studied in developing the present invention.

Generally speaking, FIG. 2A represents a scenario where an air-blast technique is implemented with a relatively high pressure or velocity air jet 200. In FIG. 2A, oil 205 is shown as the slave fluid, and air 207 is the working fluid. As shown in FIG. 2A, the fuel (i.e., oil) 205 enters the air stream or flow 207 perpendicular to the air stream or flow 207, and atomization occurs immediately or almost immediately upon entry of the slave fluid 205. Further, the surface for the slave fluid 205 (e.g., to 'A' in FIG. 2A) is not long enough for shearing purposes, thus requiring air-blasting, resulting in atomization that occurs immediately or almost immediately. Thus, in FIG. 2A, an initial droplet 206 size of the slave fluid 205 is further reduced as it becomes airborne and then is collided with the remaining working fluid (i.e., air) 207.

FIG. 2B is a diagrammatic representation of a system or apparatus according to one or more embodiments of the present invention. In contrast to FIG. 2A, the diagrammatic representation shown in FIG. 2B, directed to one or more embodiments of the present invention, uses a relatively low pressure or velocity working fluid (e.g., 'Air') 217, and a slave fluid (e.g., 'Oil') 215 that is provided parallel or substantially parallel to the working fluid 217 flow. Optionally, the slave fluid 215 may be provided at zero velocity or close to zero velocity. Alternatively, the slave fluid 215 may be provided in a non-parallel or non-substantially parallel manner, for example, perpendicular, and at zero velocity or close to zero velocity.

The slave fluid 215 can thus be provided as a liquid pre-film 215*a*, which optionally can be atomized, or alternatively outputted in the pre-film format. For example, as discussed herein, the slave fluid 215 can be provided as a liquid fuel for combustion thereof, for flame spraying, for medical therapy to coat, "plaster," "smear", or otherwise provide a therapeutic material onto the surface of a tumor within a tube or cavity, or plaque within an artery, or to identify and coat tumor tissue locations within the colon, or esophagus, for example.

The laminar flow of the slave fluid 215 can be intercepted at an angle and mixing can occur in a mixing port, which can result in uniformity or substantial uniformity of the droplet size 216. More specifically, in order to prevent pre-aeration or pre-atomization (i.e., premature aeration or atomization) of the liquid fuel film 215*a* before the film sheet reaches its minimum thickness (or a thickness prior to an intended atomization thickness), the air stream 217 can be forced through an ever decreasing flow area 210 (e.g., a non-linear 211 and/or a linear decrease 212), which can cause corresponding acceleration of the air flow toward a predetermined discharge point, for example, at an end B of a filming surface 218, thereby imparting increasing surface shear or drag, while suppressing the tendency of the film sheet 215*a* to enter the air stream until a predetermined position, i.e., at the predetermined position on the filming surface (e.g., its end, i.e., at 'B', as shown in FIG. 2B). That is, the air shearing pathway can cause the air stream to accelerate under the restriction of the reducing area 210 dimensions of the filming surface 218 relative to the air stream surface. Non-linearity, for example, of one or both surfaces can provide liquid surface disturbance suppression, as needed. Put another way, the resultant pressure exerted normal to the liquid film can increase proportionally and can dampen surface disturbances in the liquid film potentially caused by the shearing process and turbulence at an interface of the liquid film and atomizing media.

Additionally, in order to achieve a predetermined desired smallest thickness of the liquid film 215*a*, optionally, the filming surface 218 may increase in surface area in the flow direction of the working fluid 217, for example, a geometry that resembles the opening shape of a horn (e.g., a cubic or a parabolic surface expanding in area along the flow path, e.g., as seen herein in FIGS. 3, 4 and 5). Other "diverging" geometries, such as cones, may be employed for the filming surface. Further, optionally, in embodiments of the present invention, continuous suppression of air blast effects may be provided, and the velocity of the liquid fuel may not exceed the velocity of the atomizing air, for example, until portions of the liquid fuel leave the predetermined position of the filming surface 216. Thus, the surface area can allow for the axial and lateral spreading of the film 215a on the filming surface 216.

Further, the filming surface 216 is not a splash or impingement surface, but rather may be a surface which is parallel to the film 215a at all times, with sufficient cohesion and pressure gradient to drag the film 215a to near zero thickness, for example, as a result of controlling forces that minimize surface disturbance.

Optionally, in a case where an airblast is employed to some degree, the airblast can be delayed until shearing of the liquid fuel film 215a has brought the liquid to a sheet as thin as a desired diameter of a liquid droplet. Likewise, in a case where the airblast is not employed, shearing of the liquid fuel film 215a can make the sheet as thin as a desired diameter of the liquid droplet.

Once at the desired thickness and at a desired position on the filming surface 216, the sheet 215a may be intercepted by a second air flow stream or the second air flow stream can be directed through the liquid fuel sheet 215a so as to complete the air and liquid pre-mixing effect. For example, at the end of the filming surface, the liquid sheet 215a may be intersected by atomizing air or some other atomizing media 219 at an angle greater than zero and less than ninety degrees. Further, since maximum or full aeration is desired once the two atomizing media flow streams intersect, the predetermined portion of the filming surface (e.g., its end B) can be configured (geometry and/or material) to minimize adhesion and enhancing departure there from. Optionally, the angle(s) of the intersecting atomizing media flow stream 219 with respect to the fuel sheet, can determine the angle of departure as desired.

After the two air flow streams have pre-mixed fuel and air, the mixture may be ready for further processing, for example, ignition and where it can be joined by the remainder of the combustion air, for a given fuel rate. Optionally, a vaporization zone may be implemented.

Specific implementations or applications according to embodiments of the present invention will now be discussed below. In particular, a fuel injector/fuel injection apparatus, for example, for an internal combustion engine; a lean-burn pre-mix burner, for example, for industrial combustion burners; and biomedical treatment methods and devices will be described.

Fuel Injector

Generally, fuel injection involves admitting fuel into a combustion chamber of an internal combustion engine for combustion. Prior to or at entry into the combustion chamber, the fuel is atomized by the fuel injector by forcibly providing the fuel under high pressure through a nozzle.

Figure 3:
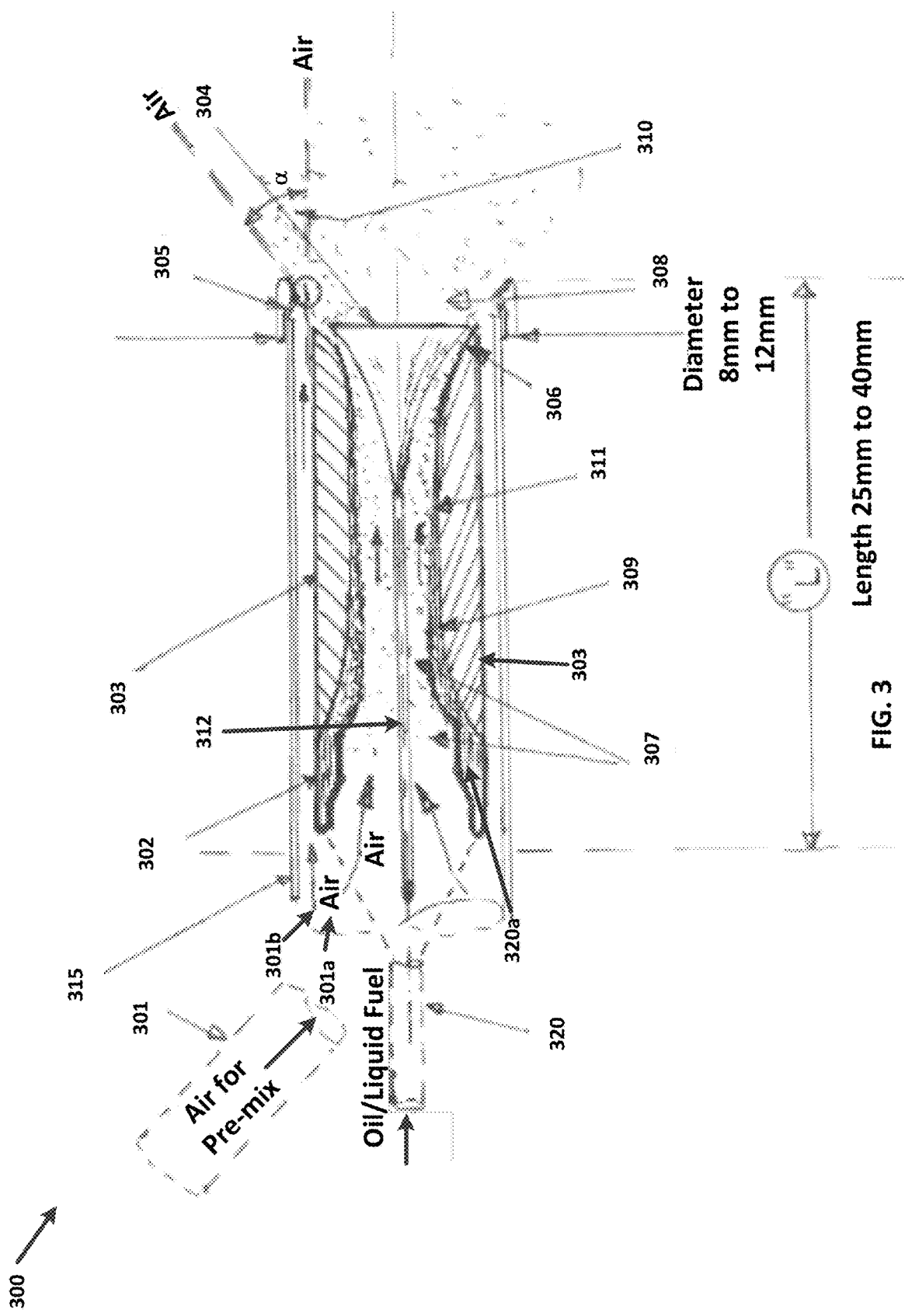
FIG. 3 is a diagrammatic representation of a fuel injector system in accordance with one or more embodiments of the present invention.

FIG. 3 shows diagrammatically a fuel injector system 300, for example, for an internal combustion engine, according to one or more embodiments of the present invention. Generally speaking, system 300 involves twin working fluids 301a, 301b (air in this case) acting upon a slave fluid 302 (a continuous laminar flow of liquid fuel in this case) on a filming surface of a predetermined length to allow delivery of the slave fluid as a sheet or mixture of micro-particles.

In particular, using air 301 as the working fluid causes the liquid fuel, "oils" or "gasolines" supplied through a fuel cavity supply body 320, for example, to deform under the viscous and pressure forces of the air, to produce a sheet of liquid fuel of a predetermined thickness at a predetermined position, resulting in pre-mixing, the atomizing and vaporizing of the fuel, and forming a premixed cloud of fuel and air. System 300 can minimize or eliminate impingement of fuel on hot surfaces, improve completeness of combustion, reduce emissions, and increase power and efficiency, without pre-atomization or prevaporization. System 300 also may not implement airblast or air jet effects and may not use micro-holes for the output of the pre-mixed cloud of fuel and air. That is, system 300 can implement an annulus or a plurality of annuli.

System 300 can include an outer air body sleeve 315 to provide air as a working fluid; the fuel cavity supply body 320 to supply liquid fuel as set forth herein, for example, as a continuous laminar flow at zero velocity and parallel to the flow of the working fluid; a filming body 303 having an inner surface upon which the liquid fuel slave fluid is provided and dragged to a predetermined thickness at a predetermined location on the filming body 303; a pintel assembly 304, which includes a pintel 306 and a stem 312; and a pre-mix body vapor tab 305. As noted, the injector has a length 'L,' for example, 25 mm to 40 mm. The working fluid (atomizing air, or other gas or liquid) can flow inside of and around the fuel supply body 302 and across an inner surface of the filming surface body 303.

The liquid fuel provided by the fuel cavity supply body 320, via an opening or openings, as a continuous laminar flow, for example, is output and provided to in inner surface of the filming body 303, where it is acted upon by the first path of the air at a beginning of a pre-mix zone 307. In this example, the liquid fuel is initially provided via the fuel cavity supply body 320 to the inner surface of the filming body 303 in a direction parallel to the filming body 303 and incidentally parallel to the flow of the first path of the air working fluid and becomes a liquid fuel film 320a. The atomizing media can be split by the presence of the pintel 306 to annularly discharge through an opening (or openings) formed thereby at an angle of departure. The pintel 306 can be positionable/re-positionable along the longitudinal axis of the system as needed.

The liquid fuel film 320a continues to be dragged along the inner surface of the filming body 303 by the shear forces of the air until compression of the film begins at 309. Optionally, the compression (i.e., pressure) forces may begin to be applied to the liquid fuel as soon as the liquid fuel exits the opening(s) of the fuel cavity supply body 320. The liquid film, subjected to shear and compression forces, is dragged to a first predetermined position 311 on the filming body 303 where the liquid fuel sheet is at a first thickness. Optionally, at the predetermined position 311, the liquid fuel film 320a can begin being simultaneously mixed with the air and vaporized. The liquid fuel film may be dragged to a second thickness at a second predetermined position later along the path of the filming surface 303, for instance, to its minimum thickness. Initial or optional additional vaporization and mixing may occur at 308 (i.e., an end of a pre-mix zone). It is also noted that the surface area of the inner surface of the filming body 303 generally expands at point 309 where compression begins to the portion on the filming body 303 where the thinnest desired portion of the liquid fuel sheet 320a is obtained. That is, in this particular embodiment, the film's surface area increases as the surface area of a horn instrument, both radially and axially.

The vaporized/atomized product may then be output at a predetermined angle based on, among other things, the geometric configuration of the filming surface at its second end and the configuration of the pintel 306. As shown in FIG. 3, the vaporized/atomized product is output or departs at a first angle. Further, the vaporized/atomized product output at the first angle is further subjected to a second path of air of the twin or duel working fluid air flows at an intersection angle $\alpha$.

Thus, for the system 300, the filming surface (i.e., the inner surface of filming body 303) may have a geometry that promotes prompt atomization at a predetermined desired position on the filming surface, when the liquid fuel sheet is thin enough to produce the smallest droplet sizes, for example, with droplets that approach molecular thickness. As such, system 300 can produce a thin cylindrical or conical sheet of atomized droplets with relatively low dissipated energy for injection into a combustion chamber, for instance.

Figure 4:
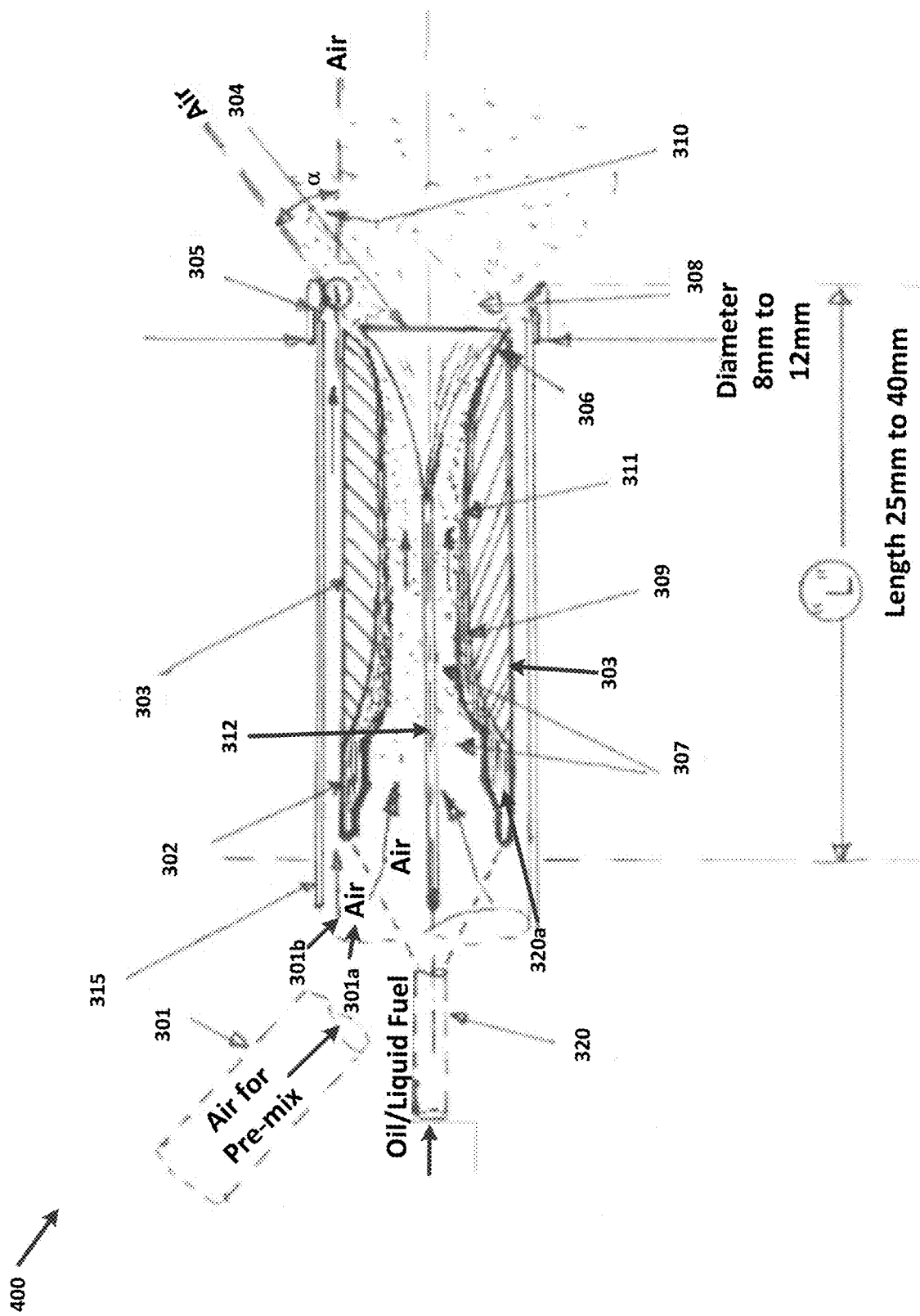
FIG. 4 is a diagrammatic representation of a variation of the fuel injector system shown in FIG. 3, in accordance with one or more embodiments of the present invention.

In an alternative embodiment, diagrammatically provided by FIG. 4, a system 400 according to one or more embodiments of the present invention can continuously instigate atomization at a predetermination position or range along a filming surface using a spiral surface area on an exterior surface of the pintel 306, for example. Optionally or alternatively, the system 400, which is essentially the same as system 300 in FIG. 3, with the exceptions that the filming surface of filming body 303 may include a spiral surface portion or portions. Thus, the geometry of pintel 306 can convert a portion of axial momentum to tangential momentum such that the cloud of premixed air and fuel may have a shortest amount or minimized amount of axial propagation.

Regarding systems 300 and 400 shown in FIG. 3 and FIG. 4, respectively, non-limiting examples of certain components are now provided. The injector systems can be provided in a body having a diameter from 8 mm to 12 mm and a length of from 25 mm to 40 mm. The pintel 306 may have an outer diameter corresponding to the diameter of the body, for example, from 8 mm to 12 mm. Further, the sizing and geometry of the injector of systems 300 and 400 can enable passage of particulate and foreign objects up to a predetermined maximum diameter (e.g., ¼" diameter). Thus, the injector systems 300 and 400 can be implemented with a mixture of fuel oil and pulverized oil, for example, in up to 50/50 ratio by weight.

Figure 5:
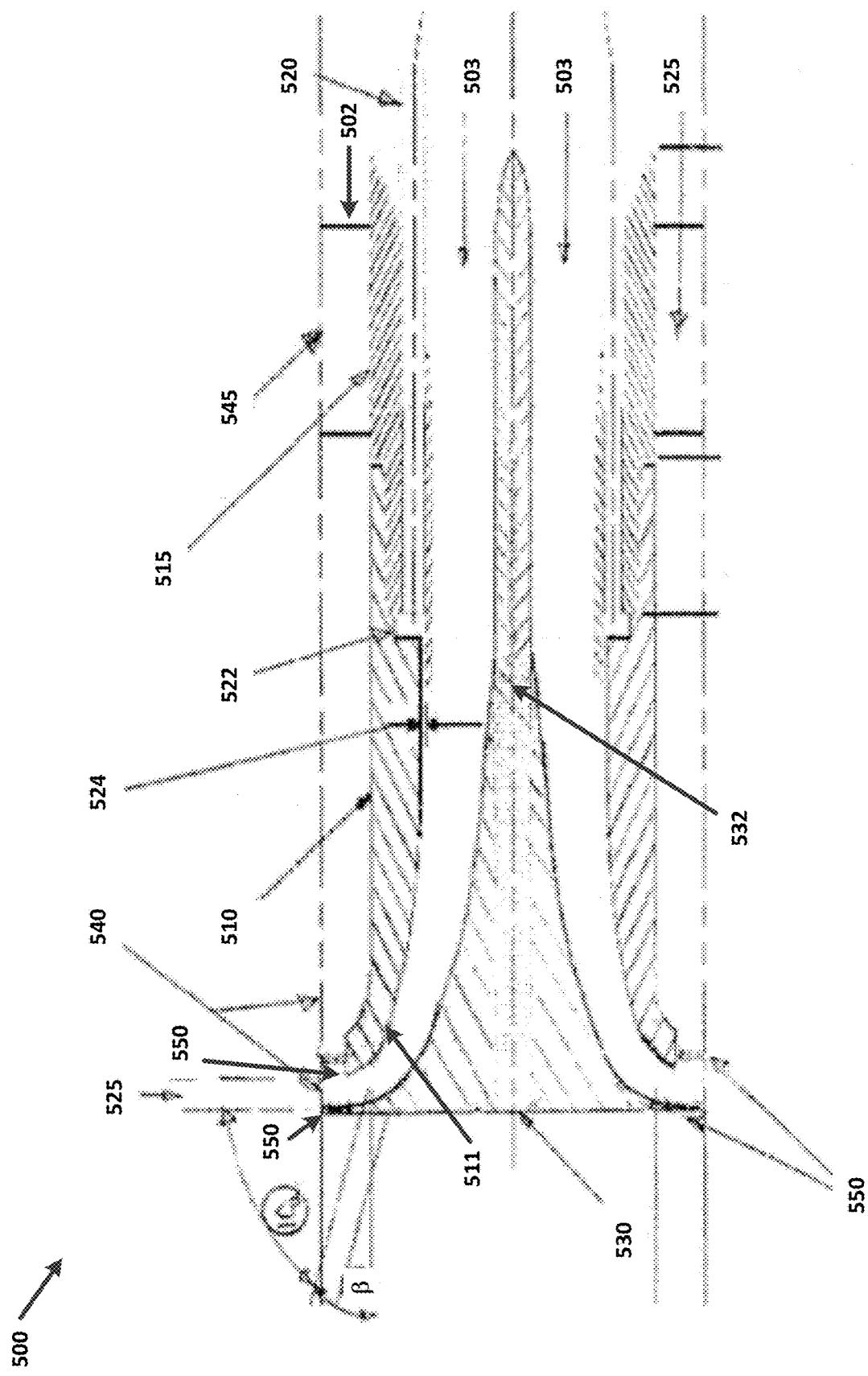
FIG. 5 is diagrammatic representation of a nozzle design for medical applications, in accordance with one or more embodiments of the present invention.

FIG. 5 is a diagrammatic representation of a nozzle design for medical applications, in accordance with one or more embodiments of the present invention. In FIG. 5, a nozzle 500 is shown that is designed for use in medical applications, for example, to apply or extract a biomedical material on a specific target within a patient's body. Specifically, the nozzle is designed to operate as a pressure device or a suction device to apply or extract medical material for arterial plaque or tumors or as a suction device to extract material, for example, it can be used to extract micro particles of plaque that might be dislodged by a laser like an "Excimer Laser". Alternatively, the laser can be used to "fix" a biomedical material, for example, a biomedical coating/netting, to the target surface.

In FIG. 5, in the nozzle 500, a first working fluid 503 flows inside of and a second working fluid 502 flows around a filming body 510 and a slave fluid body 515. The portion of the first working fluid 503 that flows inside of the filming body 510 and the slave fluid body 515 flows around a pintel 530 and a pintel stem 532 and exits through annular opening 525 at an angle of departure of β. The annular opening 525 is defined by and at the ends of the pintel 530 and the slave fluid body 515. The annular opening 525 provides an exit for an accelerating path that is defined between and along the length of the pintel 530 and the slave fluid body 515. Therefore, as the working fluid accelerates toward the annular opening 525, it imposes increasing shear and normal forces on a slave liquid 520 in a parallel slave fluid channel 522 within slave fluid body 515 and fills a slave fluid cavity 524 from which the slave fluid is then discharged through an opening 524.

When the slave fluid 520 is discharged through the opening 524 it flows onto a surface 511 of the filming body 510 as a sheet and is held in place against the surface 511 by the first working fluid 503. As the slave fluid sheet is moved toward the annular opening 525, the slave fluid sheet becomes thinner due to the normal and shear forces of the first working fluid 503. Increasing normal forces attenuate the film surface Rayleigh instabilities. Some diffusion of slave fluid sheet occurs due to the Reynolds Number differences between the first working fluid 503 and the filming body surface 511. The position of the pintel 530 can be adjusted proximally and distally using the pintel stem 532 to cause the rate of area change along the stream path to change based on the properties and dynamics of the first working fluid 503 and the slave fluid 520.

In FIG. 5, depending on the area change for the flow of the first working fluid 503 imposed upon the slave fluid 520, the slave fluid 520 can also be mixed with the first working fluid 503. The design of the wetted slave fluid surface can discourage or encourage premixing, as can its overall area.

In FIG. 5, the second working fluid 502 flows around outside surfaces of the filming body 510 and the slave fluid body 515 in either a straight path or with swirl, depending on a design of the outside surfaces of the filming body 510 and the slave fluid body 515 and intersects the slave fluid sheet or mixture adjacent to the annular opening 525 at an angle β. The flow fields of the first and second working fluids 502, 503 represent twin fluid intersections of the slave fluid at the annular opening 525, but, if the objective is to lay down a coating or netting, then, generally, only the first working fluid 503 in the center is used.

In FIG. 5, a target surface 14 is shown immediately adjacent the annular opening 525 and is, for example, an inside surface of an artery wall 545 or some other cylindrical body wall. As noted above, if the device is being used to deposit a biomedical material, only the first working fluid is used to create the desired slave fluid sheet properties for deposition. In this embodiment, an annular wiper membrane 550 extends from and around both an end of the filming body 510 and an outer perimeter edge of the pintel 530 to contact the inner surface of artery wall 545 and used for extrusion shaping of the deposited biomedical material. Alternatively, the annular wiper membrane 550 can be used to minimize the effect of the second working fluid 502.

In yet another embodiment of the present invention, the nozzle 500 can be used as a suction device to remove debris by creating a reverse flow of a working fluid to create a suction to pull debris in through the annular opening 525 and up the nozzle 500.

Lean Burn Air Pre-Mix Liquid Fuel Combustion Injector (e.g., for Burner for Industrial Combustion)

Regarding systems, methods, and apparatuses for lean burn pre-mixing, embodiments of the present invention when combusting liquid fuels so as to attenuate NOx due to some pre-vaporization of the liquid fuel to a gas, while pre-mixing it with a specific portion of total combustion air. Embodiments can be comprised of a primary combustion injector and a lean burn pre-mix liquid fuel burner. Given that a sheet or sheets of a liquid fuel slave fluid are provided due to shear and compression forces (i.e., the disclosed pressure-shear methodology) as shown and described herein, the flame that is obtained upon ignition of the liquid fuel in the foregoing provided format output from a nozzle, allows an enriched fuel/air core to a specific ratio with a lean burning outer zone, or envelope.

Systems, methods, and devices according to embodiments of the present invention regarding lean burn pre-mixing can operate under air/liquid fuel pre-mixture ratios of 25%-30%, for instance, because droplets of a predetermined diameter (e.g., as small as possible, such as, for example, 10 to 20 µm diameter droplets) may be obtained and because of the absence of "air blast" effects, until the sheet is thin enough to break up in the mixing process as it mixes with the balance of the air supplied to the nozzle.

Medical/Biomedical Device Implementation/Application

Generally speaking, in the medical/biomedical context, embodiments of the present invention use one fluid (a gas or a liquid) to work against another fluid (a liquid or a gas), in a specific way. A particular flow layer of the slave fluid or the slave fluid/working fluid mixture can be provided in a particular format with low energy, given that the fluid/fluid mixture can be provided at relatively low velocity and momentum. For example, utilizing a working fluid consistent with a particular application or environment, a sheet or sheets of a slave biomedical material under low velocity effects, can be extruded or coated onto a target surface.

Embodiments of the present invention can be implemented in any tubular or cavitous part of the body to achieve a particular medical or biomedical purpose, such as treating plaque, tumors, etc. External applications are also implemented. Thus, the slave fluid (or slave fluid-working fluid mixture) can be applied topically, for example, as a surface coating or for encapsulation. For example, the "working fluid" (e.g., blood in an artery, a wash, or a chemical agent), can cause another fluid to deform under the viscous and pressure forces of the former to produce a sheet, net, or film of the slave fluid. The resultant slave fluid and optionally a mixture of the slave fluid and the working fluid can be output so as to be applied to a surface of arterial plaque, for instance, or tumor tissue within the body. Further, a desired thickness can be achieved for the surface treatment or encapsulation, and the slave fluid/slave fluid mixture can have a rapid attachment affinity depending upon the local environment and a desired action. Additionally, the slave fluid/slave fluid mixture can have properties to allow gradual dissipation and/or containment or consumption regarding its host.

While the invention(s) has/have been described in conjunction with a number of embodiments, it is evident that many alternatives, modifications and variations would be or are apparent to those of ordinary skill in the applicable arts. Accordingly, Applicant intends to embrace all such alternatives, modifications, equivalents, and variations that are within the spirit and scope of the invention(s) described herein.

What is claimed is:

1. A method, comprising:
   providing a viscous liquid prior to atomization in a first continuous laminar film format on an inner surface of a filming body;
   providing a first working fluid, the first working fluid including air; and
   transforming the viscous liquid in the first continuous laminar film format to a second format on the inner surface of the filming body using at least the first working fluid.

2. The method according to claim 1, wherein the viscous liquid is a liquid fuel.

3. The method according to claim 1, wherein the viscous liquid is a petroleum-derived liquid.

4. The method according to claim 3, wherein the viscous liquid is oil.

5. The method according to claim 3, wherein the viscous liquid is gasoline.

6. The method according to claim 1, wherein the first working fluid is blood.

7. The method according to claim 1, wherein the viscous liquid includes a chemical agent, a biological agent, and/or vesicles.

8. The method according to claim 7, wherein the first working fluid is blood.

9. The method according to claim 1, wherein the second format is a relatively thin sheet.

10. The method according to claim 9, wherein the thin sheet is one of flat, cylindrical, half or partial toroidal, arced, curved, linear, or non-linear.

11. The method according to claim 9, wherein the thin sheet takes the form of the inner surface of the filming body.

12. The method according to claim 11, wherein the viscous liquid in the second format is for atomizing.

13. The method according to claim 12, wherein the viscous liquid in the second format is for mixing with air.

14. The method according to claim 13, wherein the mixing with air is premixing.

15. The method according to claim 1, further comprising transforming the viscous liquid from the second format to a third format using at least the first working fluid.

16. The method according to claim 15, wherein the transforming to the third format uses the first working fluid and a second working fluid.

17. The method according to claim 16, wherein the second working fluid is air.

18. The method according to claim 17, wherein the first and second working fluids are intersecting or parallel streams of air.

19. The method according to claim 1, wherein the viscosity of the viscous fluid is at or below 200 Saybolt Universal Seconds (SSU).

20. The method according to claim 1, wherein the second format of the viscous liquid is a sheet or a mixture of micro-particles.

21. The method according to claim 1, wherein a predetermined thickness of the viscous liquid in the second format is 10 to 20 microns, and such thickness is achieved immediately prior to atomization.

* * * * *